United States Patent [19]

Henn et al.

[11] Patent Number: 4,831,197
[45] Date of Patent: May 16, 1989

[54] PROCESS FOR THE CONTINUOUS PRODUCTION OF LOWER ALIPHATIC ALCOHOLS

[75] Inventors: Friedrich Henn, Duisburg; Wilhelm Neier, Rheinberg; Gunter Strehlke, Duisberg; Werner Webers, Rheinberg, all of Fed. Rep. of Germany

[73] Assignee: Deutsche Texaco Aktiengesellschaft, Hamburg, Fed. Rep. of Germany

[21] Appl. No.: 92,104

[22] Filed: Sep. 2, 1987

Related U.S. Application Data

[63] Continuation of Ser. No. 844,654, Mar. 27, 1986, abandoned.

[30] Foreign Application Priority Data

Apr. 6, 1985 [DE] Fed. Rep. of Germany ....... 3512518

[51] Int. Cl.$^4$ ................. C07C 29/04; C07C 31/10; C07C 31/12; C07C 31/125
[52] U.S. Cl. .................................................. 568/899
[58] Field of Search ......................................... 568/899

[56] References Cited

U.S. PATENT DOCUMENTS

| | | | |
|---|---|---|---|
| 3,994,983 | 11/1976 | Webers et al. | 568/899 |
| 4,012,456 | 3/1977 | Chaplits | 568/899 |
| 4,340,769 | 7/1982 | Brandes et al. | 568/899 |
| 4,476,333 | 10/1984 | Neier et al. | 568/899 |

OTHER PUBLICATIONS

Starks et al, "Phase Transfer Catalysis" (1978) Academic Press Inc., p. 5.

Primary Examiner—J. E. Evans
Attorney, Agent, or Firm—James J. O'Loughlin; Robert A. Kulason; Thomas H. Whaley

[57] ABSTRACT

An improved process for the production of lower aliphatic alcohols by the catalytic hydration of a lower aliphatic olefin in the presence of a strongly acidic cation exchange resin catalyst in a fixed bed reactor and in which a cationic surfactant has been added to the process water is provided.

8 Claims, 2 Drawing Sheets

4,831,197

PROCESS FOR THE CONTINUOUS PRODUCTION OF LOWER ALIPHATIC ALCOHOLS

This is a continuation, of application Ser. No. 844,654, filed Mar. 27, 1986, now abandoned.

BACKGROUND OF THE INVENTION

The invention relates to a process for the continuous production of a lower aliphatic alcohol having from 3 to 5 carbon atoms by the catalytic hydration of a lower aliphatic olefin with 3 to 5 carbon atoms in the presence of water and a strongly acidic cation exchange resin catalyst in a fixed bed reactor at a temperature of about 120°–180° C. and a pressure of about 40–200 bar, with removal of the product stream, separation of the alcohol from the product stream and recycling of the process water.

DISCLOSURE STATEMENT

Processes for producing lower aliphatic alcohols from the corresponding olefins have been known and are described in German patent specification Nos. 22 33 967 and 24 29 770, corresponding to U.S. Pat. Nos. 4,340,769 and 3,994,983, respectively, and are particularly used for producing isopropyl alcohol (IPA), sec. butyl alcohol (SBA), and tert. butyl alcohol (TBA).

When effecting the hydration of n-butenes according to the process described in DE-PS No. 24 29 770 and recycling the process water as described in DE-PS No. 30 40 997, corresponding to U.S. Pat. No. 4,476,333, the differential pressure between reactor sump and reactor head gradually increases during the operation of the process. After about 400 hours in the operation of the process, substantial pressure shocks occur within the reactor due to plugging which forces a shut down of the reactor. The reactor must then be cleaned out before restarting the process.

Attempts to solve this problem by continuously recycling the process water and/or by the use of fresh water have not been successful. Likewise, treatment of the process water being recycled using ion exchange resins does not result in an improvement with respect to lowering or controlling the differential pressure in the reactor.

In the trickle type process scheme described in DE-PS No. 22 33 967, distribution problem also exist. Indeed, hot spots have been observed in the reactor which results in an objectionable odor in the distilled isopropyl alcohol. It is postulated that during the start-up phase, side reactions take place at particularly reactive sites on the catalyst which in combination with a poor distribution of the water results in incineration of catalyst areas and lump formation. The evidence indicates that a better distribution of the reactants is necessary particularly when starting the reactor after filling it with fresh catalyst.

The disclosures in U.S. Pat. No. 4,340,769, 3,994,983, and 4,476,333 are incorporated herein by reference.

It is the object of the present invention to effect the direct hydration of lower aliphatic olefins in such a way that the reactants are more evenly distributed on the catalyst so that the differential pressure within the reactor is reduced or stabilized at a relatively low level.

SUMMARY OF THE INVENTION

According to the invention, an improved process is provided by adding a cationic surfactant to the reaction mixture, which is stable under the reaction conditions, and maintaining the surfactant concentration in the aqueous solution from about 0.1 to 100 parts of surfactant per million parts of the aqueous solution.

According to a preferred embodiment of the process, the catalyst is arranged in a fixed bed and at least one reaction component is passed through the reactor from the bottom to the top. The gaseous phase is removed at the reactor head, and the alcohol produced is separated from the gaseous phase by partial pressure release.

It was very surprisingly to find that the the differential pressure in the reactor does not increase significantly if a small amount of a cationic surfactant, particularly the quaternary ammonium compounds, is added to or maintained in the process water for the reactor.

Non-ionic or anionic surfactants do not produce this effect. Anionic surfactants on the contrary have an adverse effect. When an anionic surfactant is added to the process water, the differential pressure increases further. Organic solvents are not used in the instant process.

For the implementation of the process of the invention, cationic surfactants which are stable, particularly temperature stable, under the reaction conditions for the direct hydration of olefins are suitable. In general, the preferred class of cationic surfactants can be represented by the formula: $RR_1R_2R_3NCl$ in which $R$, $R_1$, $R_2$ and $R_3$ each represent a hydrocarbyl or alkanoyl radical having from 1 to 18 carbon atoms. Examples of suitable cationic surfactants include:

dimethyl distearyl ammonium chloride
trimethyl palmityl ammonium chloride
cetyl trimethyl ammonium chloride
lauryl dimethyl benzyl ammonium chloride
oxyethyl alkyl ammonium phosphate Alkanol ammonium salts, pyridinium salts, imidazoline salts, oxazolinium salts, thiazolinium salts, salts of aminoxides, sulfonium salts, quinolinium salts, isoquinolinium salts, tropylium salts may also be effective. However, their temperature stabilities may be lower than those of the noted ammonium compounds. Dimethyl distearyl ammonium chloride has proven to be most effective and has the added advantage of having good temperature stability.

It was particularly surprising that the improvement occurs at very low surfactant concentrations. A quantity of 4–10 ppm of surfactant continuously added to or maintained in the process water substantially lowered the differential pressure in the reactor and maintained a low pressure differential in the reactor through the reaction. In general, the cationic surfactant can constitute from about 0.1 to 100 parts of surfactant per million parts of the aqueous solution with a preferred range being from about 2 to 40 parts of surfactant per million parts of the aqueous solution.

Normally, the cationic surfactants deactivate the cationic exchangers. However, it was found that the effective dosage of the cationic surfactant used is so low that no measurable deactivation of the strongly acidic cation exchanger used as a catalyst is observed. On the contrary, a number of positive effects are realized, such as a better distribution of the reactants on the catalyst and stabilization of the differential pressure at a low level, which make processes for producing lower aliphatic alcohols more economical by improving selectivity and product quality. The addition of the cationic surfactant achieves a better distribution of the reaction phases on the catalyst grains. This is shown in the production of sec. butyl alcohol by the lowering of the amount of di-sec. butyl ether (SBE) produced from about 4 parts by weight to 1 part by weight, relative to sec. butyl alcohol. Separation into a gaseous and a liquid phase at the reactor head is also improved. The formation of foam generally observed at a high cross-sectional gas load is completely suppressed and the crude alcohol obtained is free from acid traces entrained from the process water with the foam.

The following examples illustrate embodiments of the invention conducted according to the procedures illustrated in the attached FIGS. 1 and 2.

The following Examples illustrate the process of the invention including detailed description of the drawings.

COMPARISON EXAMPLE 1

Figure 1:
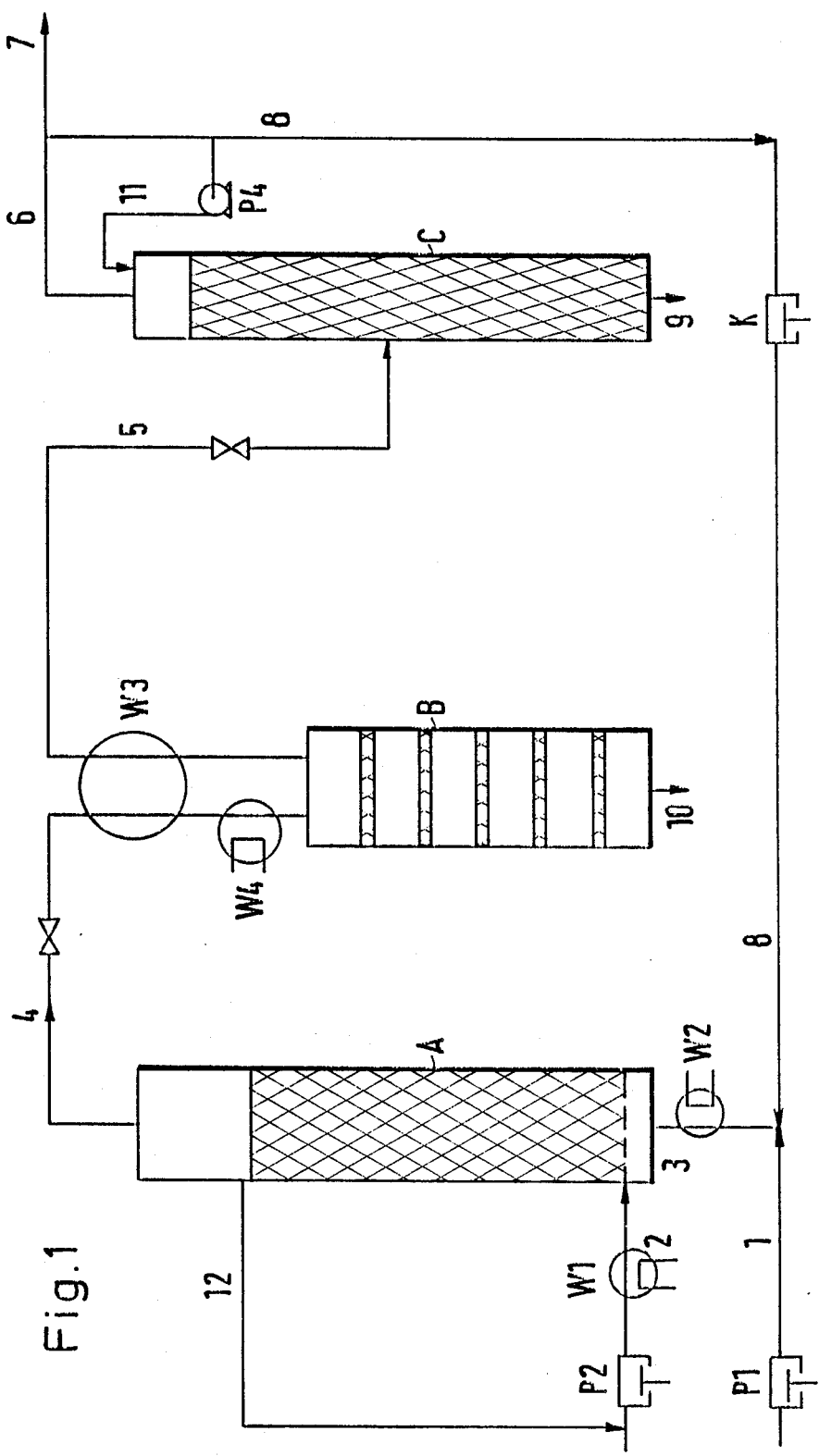
FIG. 1 is a flow sheet for implementation of a sump phase process according to DE-PS No. 30 40 997.

The reaction A depicted in FIG. 1 had a diameter of 500 mm and a length of 10.0 m. It was packed with 1,700 l of a strongly acidic ion exchanger. The differential pressure over the reactor length was observed by differential pressure measuring.

To the reactor 300.3 kgs/h of a n-butene/butane mixture containing 85% n-butene (4,534 moles of n-butene) and having been presaturated with 1.5% water were charged via line 1 and 204 kgs/h of demineralized water (11,333 moles of $H_2O$) were charged via line 1. In heat exchanger W1 the water was preheated at a temperature of 155°–160° C. The feed gas charged via line 1 by means of dosing pump P1 was mixed with the recycle gas recycled via line 8 and evaporated in evaporator W2, was heated at a temperature of 160° C., and was charged to the sump of the reactor via line 3. In the reactor a reaction pressure of 60 bar was maintained. At the head of the reactor the vaporous sec. butyl alcohol formed was removed together with excess $C_4$ gas via line 4, was subjected to pressure release, was liquefied, and was led via heat exchangers W3 and W4 through separator B. The separated water is removed via line 10 and is recharged as part of the process water via line 2. The liquid n-butane/n-butene mixture is revaporized by exchange in heat exchanger W3 and is charged via line 5 to pressurized column C where it is split up into alcohol and reaction gas. The alcohol is removed via line 9. Most of the excess n-butane/n-butene mixture (2,700 kgs/h) was recharged via line 8 to the reactor by means of compressor K. Part of the stream was phased out as residual gas via line 7. Using pump P4 a small recycle 11 is fed to the column.

The following results were obtained:

| Operating Time, days | Differential Pressure, bar | SBA Quantity, kg/h | SBE Quantity, kg/h |
| --- | --- | --- | --- |
| 1 | 2.4 | 202 | 2.0 |
| 3 | 3.5 | 190 | 2.7 |
| 5 | 3.7 | 188 | 3.1 |
| 7 | 3.7 | 189 | 3.0 |

-continued

| Operating Time, days | Differential Pressure, bar | SBA Quantity, kg/h | SBE Quantity, kg/h |
| --- | --- | --- | --- |
| 9 | 3.6 | 190 | 3.2 |
| 10 | 3.8 | 188 | 3.0 |

Legend:
SBA = sec. butyl alcohol
SBE = di-sec. butyl ether

At separator B approximately 55 kgs/h of an aqueous phase were obtained with stream 10.

COMPARISON EXAMPLE 2

The process described in comparison Example 1 was repeated, the difference being that process water removed at the head was recharged to the reactor sump. Most of the process water, approximately 96%, was recycled via line 12. Approximately 4% of the process water was recycled via line 10. While the other conditions were the same, the following results were obtained:

| Operating Time, days | Differential Pressure, bar | SBA Quantity, kg/h | SBE Quantity, kg/h |
| --- | --- | --- | --- |
| 1 | 2.7 | 203 | 2.1 |
| 3 | 3.6 | 189 | 2.9 |
| 5 | 6.7 | 181 | 5.8 |
| 7 | 8.9 | 174 | 7.8 |
| 9 | 9.6 | 171 | 8.6 |
| 10 | 10.1 | 171 | 8.8 |

After the pressure was released to 1 bar and the feeding of gas was stopped, the catalyst was washed for 24 hours with pure water.

After continuation Of the test run the following results were obtained:

| Operating Time, days | Differential Pressure, bar | SBA Quantity, kg/h | SBE Quantity, kg/h |
| --- | --- | --- | --- |
| 11 | 2.9 | 202 | 2.3 |
| 13 | 3.9 | 188 | 3.1 |
| 15 | 7.2 | 179 | 6.0 |
| 17 | 9.3 | 172 | 8.1 |
| 19 | 10.1 | 170 | 8.7 |
| 20 | 10.8 | 169 | 9.0 |

Approximately 80 kgs/h of an aqueous phase were removed via stream 10.

EXAMPLE 1

Comparison Example 2 was repeated, the difference being that before pump P2 8 g/h of a 20% solution of dimethyl distearyl ammonium chloride were added to the process water stream (204 kgs/h). Thus, the process water had a surfactant concentration of 4 ppm. 70 to 80% of the surfactant quantity remained on the catalyst.

The following results were obtained:

| Operating Time, days | Differential Pressure, bar | SBA Quantity, kg/h | SBE Quantity, kg/h |
| --- | --- | --- | --- |
| 1 | 0.6 | 208 | 1.9 |
| 3 | 0.8 | 207 | 1.8 |
| 5 | 0.7 | 207 | 1.7 |
| 7 | 0.7 | 208 | 1.8 |
| 9 | 0.8 | 207 | 1.8 |

-continued

| Operating Time, days | Differential Pressure, bar | SBA Quantity, kg/h | SBE Quantity, kg/h |
| --- | --- | --- | --- |
| 11 | 0.8 | 208 | 1.9 |
| 15 | 0.7 | 208 | 1.8 |
| 20 | 0.8 | 208 | 1.8 |
| 30 | 0.8 | 207 | 1.8 |

EXAMPLE 2

Example 1 was repeated, the difference being that the dosage of the 20% solution of the cationic surfactant was increased to 80 g/h. During an operating time of 30 days the same results as in Example 1 were obtained.

COMPARISON EXAMPLE 3

Figure 2:
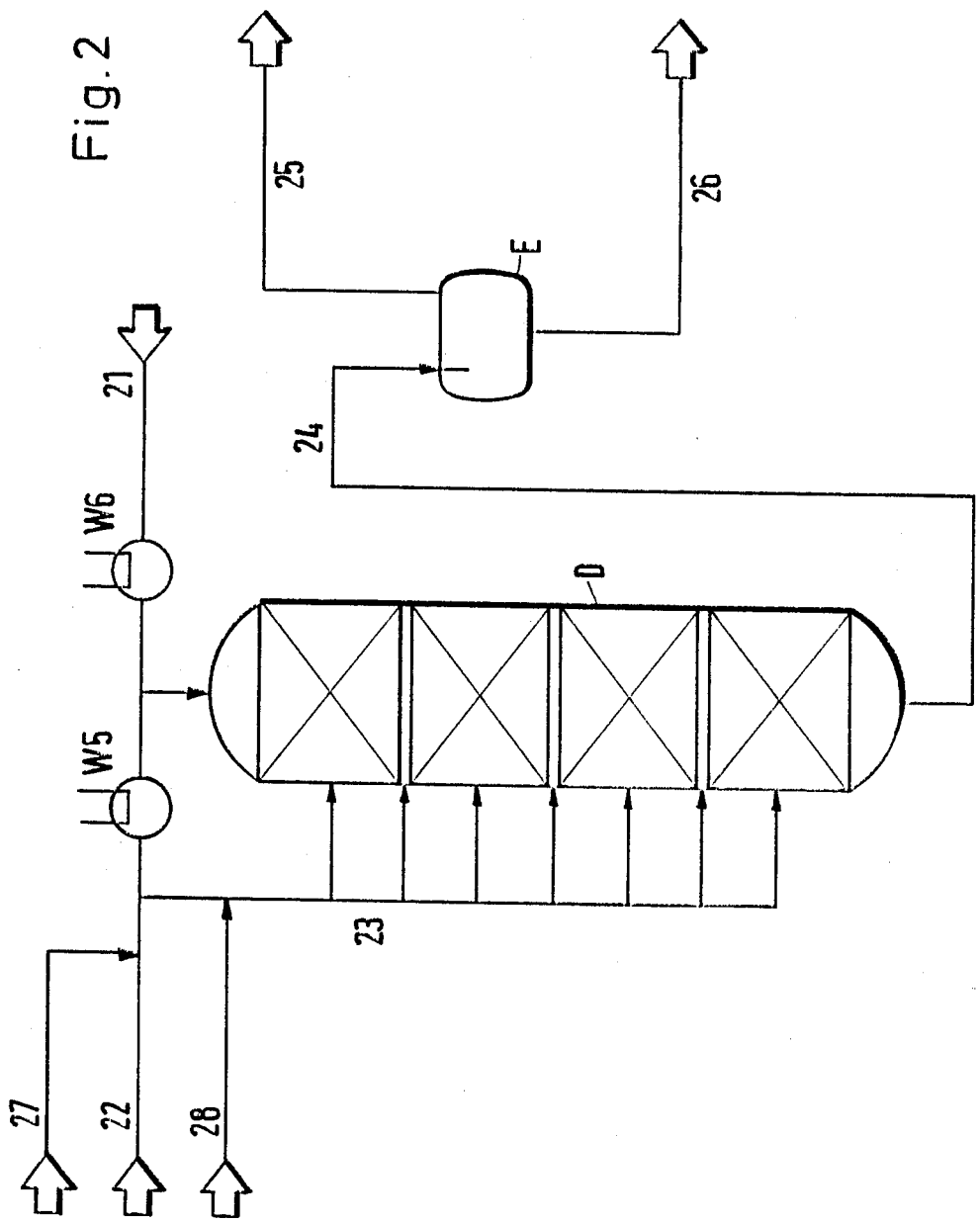
FIG. 2 is a flow sheet for implementation of a trickle process according to DE-PS No. 22 33 967.

The reactor D depicted in FIG. 2 has a diameter of 500 mm and a length of 10 m. It was packed with 1,700 liters of a strongly acidic cation exchanger. To remove the reaction heat part of the reaction water was charged to separate places of the catalyst bed, as described in German patent specification No. 21 47 739. The differential pressure over the reactor length was observed by differential pressure measuring.

To the reactor 331 kgs/h of a propene/propane mixture containing 92% propene (7,250 moles of propane) were charged via line 21 and 2,475 kgs/h of demineralized water (137.5 k moles of $H_2O$) were charged via line 22. Part of the water was preheated at 140° to 145° C. in heat exchanger W5. To remove the reaction heat another portion (approximately 25%) was charged to different places of the reactor without being preheated. The feed gas charged via line 21 was evaporated in vaporizer W6 and was charged together with the reaction water to the reactor head. In the reactor a reaction pressure of 100 bar was established. Via line 24 the aqueous isopropyl alcohol was charged together with the excess reaction gas to separator E. After separation of the gaseous phase (removal via line 25) 2,690 kgs/h of an aqueous isopropyl alcohol containing 295 kgs of isopropyl alcohol and 25.6 kgs of diisopropyl ether were obtained via line 26. The catalyst efficiency was 2.89 moles of IPA/liter of catalyst an hour, the selectivity was 92%. Over the reactor length a differential pressure of 3.5 to 4.0 bar was measured.

EXAMPLE 3

Comparison Example 3 was repeated under the same conditions except that through the lines 27 and 28 62 g/h were charged to line 22 and another 62 g/h of a 20% solution of dimethyl distearyl ammonium chloride in isopropyl alcohol were charged to line 23.

By this measure the differential pressure decreased to 1.6–2.0 bar over the reactor length. The amount of isopropyl alcohol produced increased to 327 kgs/h, and the amount of ether formed decreased to 15.0 kgs/h.

The catalyst efficiency now was 3.20 moles of IPA/liter of catalyst an hours, the selectivity was 95.6%.

We claim:

1. In a process for the continuous production of an aliphatic alcohol having from 3 to 5 carbon atoms by the catalytic hydration of an aliphatic olefin having 3 to 5 carbon atoms in the presence of water and a strongly acidic cation exchange catalyst in a fixed bed reactor at a temperature from about 120°–180° C. and a pressure from about 40–200 bar, and in the absence of any added organic solvent with removal of the product stream, separation of the alcohol from the product stram and recycling of the process water, the improvement which comprises adding a cationic surfactant to the process water to form an aqueous solution which is stable under the process conditions and maintaining the concentration of the surfactant in the aqueous solution in the range from about 0.1 to 100 parts of surfactant per million parts of the aqueous solution.

2. A process according to claim 1 in which the concentration of the surfactant it maintained in a range from about 2 to about 40 parts of surfactant per million parts of said aqueous solution.

3. A process according to claim 1 in which the concentration of said surfactant is maintained in a range from about 4 to about 10 parts per million parts of said aqueous solution.

4. A process according to claim 1 in which said surfactant is a quaternary ammonium compound.

5. A process according to claim 1 in which surfactant is dimethyl distearyl ammonium chloride.

6. A process according to claim 1 in which said process is conducted by passing at least one reaction component from the bottom to the top of said fixed bed reactor, removing the gaseous phase at the head of the reactor and separating the alcohol from the gaseous phase by partial pressure release.

7. A process according to claim 1 in which said surfactant is a quaternary ammonium compound represented by the formula:

$RR_1R_2R_3NCl$ in which

R, $R_1$, $R_2$ and $R_3$ represent hydrocarbyl and alkanoyl radicals having from 1 to 18 carbon atoms.

8. A process according to claim 7 in which R, $R_1$ and $R_2$ represent alkyl radicals and $R_3$ represents an alkanoyl radical having from 12 to 18 carbon atoms.

* * * * *